(12) United States Patent
Dau et al.

(10) Patent No.: US 11,760,026 B2
(45) Date of Patent: Sep. 19, 2023

(54) INSTRUMENTED INTRA-ORAL APPLIANCE COMPUTATIONALLY DESIGNED FOR OPTIMIZED FITTING AND FUNCTIONALITY

(71) Applicant: Biomechanics Consulting and Research, LLC, Charlottesville, VA (US)

(72) Inventors: Nathan Dau, Palmyra, VA (US); Rich Rydin, Chapel Hill, NC (US); Jeff Crandall, Charlottesville, VA (US)

(*) Notice: Subject to any disclaimer, the term of this patent is extended or adjusted under 35 U.S.C. 154(b) by 1380 days.

(21) Appl. No.: 16/156,499

(22) Filed: Oct. 10, 2018

(65) Prior Publication Data
US 2019/0105842 A1 Apr. 11, 2019

Related U.S. Application Data

(60) Provisional application No. 62/570,124, filed on Oct. 10, 2017.

(51) Int. Cl.
| | |
|---|---|
| *B29C 64/386* | (2017.01) |
| *A61C 9/00* | (2006.01) |
| *A61B 5/00* | (2006.01) |
| *B33Y 80/00* | (2015.01) |
| *A61C 19/06* | (2006.01) |

(Continued)

(52) U.S. Cl.
CPC .......... *B29C 64/386* (2017.08); *A61B 5/682* (2013.01); *A61C 9/004* (2013.01); *A61C 9/0046* (2013.01); *A61C 9/0053* (2013.01); *A61C 19/066* (2013.01); *A63B 71/085* (2013.01); *B33Y 10/00* (2014.12); *B33Y 50/00* (2014.12); *B33Y 80/00* (2014.12); *G06F 30/17* (2020.01); *G06T 7/0012* (2013.01); *A61B 5/0205* (2013.01); *A61B 2562/12* (2013.01); *A61C 13/0004* (2013.01); *A63B 2209/00* (2013.01); *G06T 2207/30036* (2013.01)

(58) Field of Classification Search
CPC ..... B29C 64/386; A61B 5/682; A61B 5/0205; A61B 2562/12; A61C 9/004; A61C 9/0046; A61C 9/0053; A61C 19/066; A61C 13/0004; A63B 71/085; A63B 2209/00; A63B 2220/30; A63B 2220/40; A63B 2220/53; A63B 2220/80; A63B 2225/20; A63B 2230/10; A63B 2230/207; A63B 2230/50; A63B 2220/833; A63B 2225/50; A63B 2230/06; A63B 2230/202; B33Y 10/00; B33Y 50/00; B33Y 80/00; G06F 30/17; G06T 7/0012; G06T 2207/30036

See application file for complete search history.

(56) References Cited

U.S. PATENT DOCUMENTS

| | | | |
|---|---|---|---|
| 10,893,918 B2* | 1/2021 | Borovinskih | G16H 50/50 |
| 2010/0014689 A1* | 1/2010 | Kassayan | H04R 1/083 |
| | | | 381/151 |

(Continued)

FOREIGN PATENT DOCUMENTS

| | | | | |
|---|---|---|---|---|
| GB | 2470279 A | * | 11/2010 | G11B 33/06 |

*Primary Examiner* — Walter L Lindsay, Jr.
*Assistant Examiner* — Frederick Wenderoth
(74) *Attorney, Agent, or Firm* — Woods Rogers Vandeventer Black PLC; Nathan A. Evans

(57) ABSTRACT

A computationally-designed instrumented intra-oral appliance to optimize the location and coupling of sensors to optimize data integrity while maximizing comfort for the wearer.

13 Claims, 4 Drawing Sheets

Exemplary rigid layers thermoformed of 1.5 mm Biocryl depicting the location of the electronics geometries in grey for sample 2 (A) and sample 3 (B).

(51) Int. Cl.
*B33Y 10/00* (2015.01)
*B33Y 50/00* (2015.01)
*A63B 71/08* (2006.01)
*G06F 30/17* (2020.01)
*G06T 7/00* (2017.01)
A61B 5/0205 (2006.01)
A61C 13/00 (2006.01)

(56) References Cited

U.S. PATENT DOCUMENTS

2010/0098270 A1* 4/2010 Abolfathi ............... G01P 1/127
 2/463
2017/0095204 A1* 4/2017 Stitzel, Jr. .............. A61B 5/682
2018/0263737 A1* 9/2018 Simmonds ............. G16H 10/60
2019/0388189 A1* 12/2019 Shivapuja .............. A61C 7/002

* cited by examiner

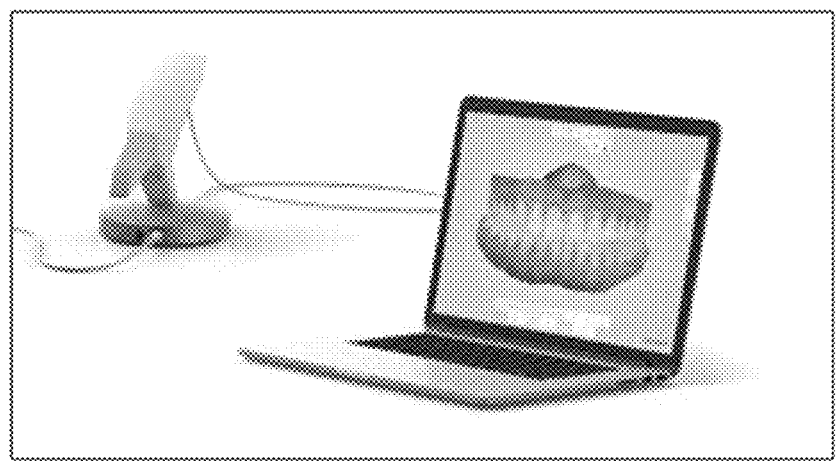
Figure 1: 3Shape Trios intra-oral scanning pod.

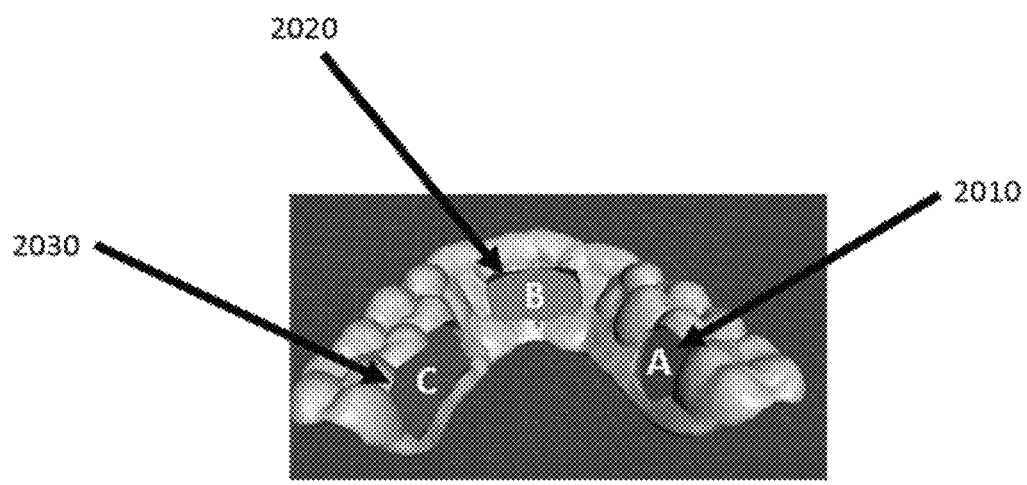
Figure 2: Three electronics geometries including the battery (A), the main circuit board (B), and the power circuit board (C).

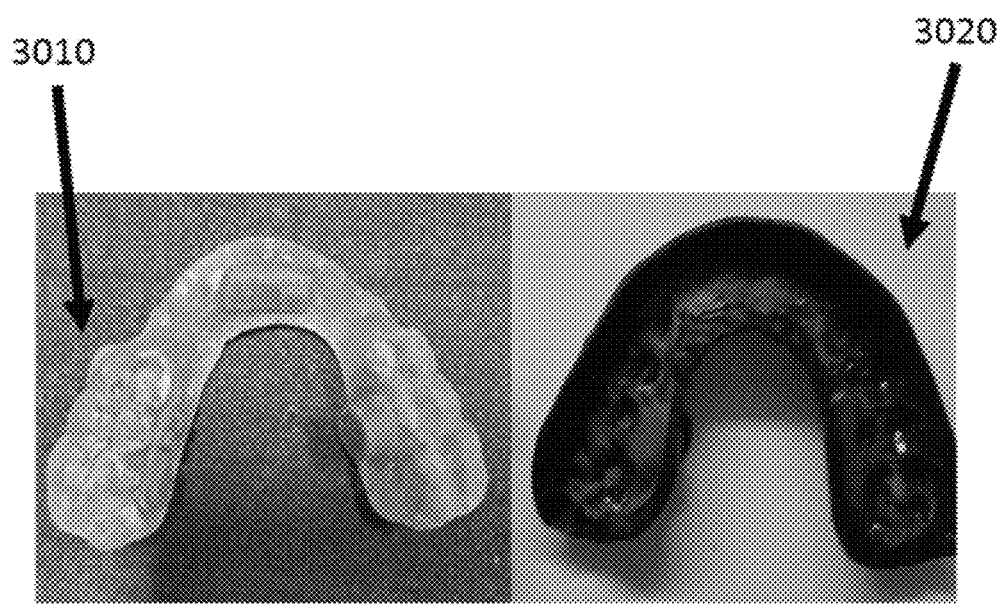
Figure 3: Sample 1 with the rigid 3D printed layer and electronics geometries (3010) and the completed sample with trimmed EVA (3020).

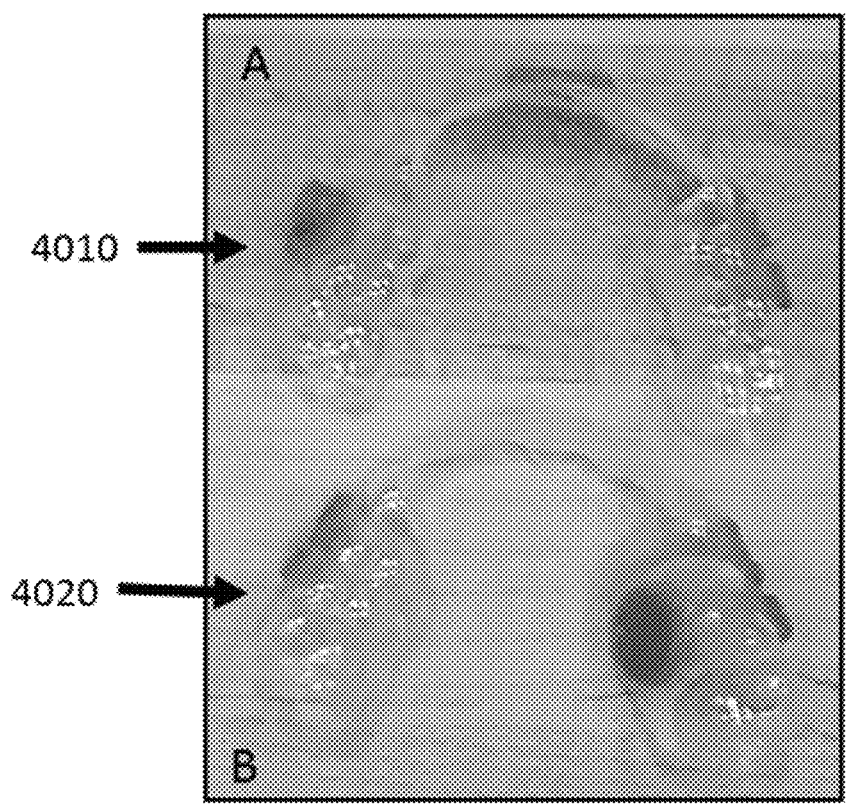
Figure 4: Exemplary rigid layers thermoformed of 1.5 mm Biocryl depicting the location of the electronics geometries in grey for sample 2 (A) and sample 3 (B).

INSTRUMENTED INTRA-ORAL APPLIANCE COMPUTATIONALLY DESIGNED FOR OPTIMIZED FITTING AND FUNCTIONALITY

CROSS-REFERENCE TO RELATED APPLICATION

The present application relies on the disclosures of and claims priority to and the benefit of the filing date of U.S. Provisional Application No. 62/570,124, filed Oct. 10, 2017. The disclosures of that application are hereby incorporated by reference herein in their entireties.

BACKGROUND

Field of the Invention

The present invention is directed to a custom instrumented intra-oral appliance that is designed to increase compliance by the wearer. It is also designed such that the sensor locations are optimized to accurately record human performance data or health metrics, including but not limited to, blood oxygen level, heart rate, head kinematics, etc. In one embodiment, sensors are strategically placed in optimal location(s) to record and/or evaluate head kinematics experienced during impact events, with an emphasis on avoiding recording false positives.

In another embodiment, a near infrared sensor is located over or near a superficial artery to record heart rate, blood oxygen level, blood osmolality, blood glucose, etc. with an emphasis on mitigating data artifacts caused by human motion and ambient light interference. In one aspect, heart rate and activity data from one or more sensors in or on the oral appliance may be combined with known wearer physiologic metrics, including height, weight, gender, age, and ethnicity, in order to determine accurate caloric expenditure. In one embodiment, an activity sensor could be added to monitor motion of the wearer. The combination of the near infrared and activity sensors could be used to monitor sleep and the effectiveness of the designed appliance.

In another embodiment, sensors are located to record the flow and quality of gases being inhaled into and/or exhaled from the body with an emphasis on minimizing the resistance of flow or generating turbulent flow that induces measurement errors. In one embodiment, the air flow sensor could be combined with near infrared and activity sensors to create an at home sleep test.

In another embodiment, the sensors are strain gauges that are located in a retainer or orthodontic aligner in locations of the device that apply forces on the teeth to quantify the duration and magnitude of the reaction forces on the device.

In another embodiment, rigid electronic components are located based on size and shape compared to the wearer's unique teeth and mouth geometry in order to increase comfort and enhance the accuracy of recording desired parameters, and the electrical connections between the electronic components are accomplished using a flexible, conductive material that can be manufactured within the appliance to allow electronics to be placed at unique distances and locations from one another depending on the configuration or shape of each particular wearer's particular device.

In another embodiment of the present invention, an intra-oral appliance is provided that is designed utilizing an intra-oral scan of the wearer where the intra-oral scan provides data that facilitates designing the device in computational space.

In one embodiment, the data from the intra-oral scan is used to design a comfortable appliance that avoids contacting sensitive areas including those affected by gum disease. In another embodiment, the data from the intra-oral scan is used to identify surface geometry that best matches the sensors and electronics to be placed into the appliance. In another embodiment, the data from the intra-oral scan are used to define optimal contact areas for securing the device in place. Additionally, this could be used to minimize the volume or surface area of the device while maintaining an acceptable level of device retention.

In another embodiment of the present invention, an intra-oral appliance is provided that is designed utilizing an extraoral scan of a dental model of the wearer where the extraoral scan provides data that facilitates designing the device in computational space.

The present invention is directed to a custom intra-oral appliance that is designed and optimized computationally. The design of a general device could be optimized using scans from the target population for the device using a statistical shape analysis (SSA). Further, each device could be designed specifically for individual users based on a general instrumentation design defined by the SSA and a best fit to the individual anatomy.

In another embodiment of the present invention, a method for making an intra-oral appliance is provided whereby the custom intra-oral appliance is built in part or in whole using 3D printing. In another embodiment of the present invention, a method for locating and orientating the sensors with respect to the head center of gravity is taught using 3D data from an intra-oral scan and a surface scan, a still image, or another form of imaging such as X-ray or CT Scan.

Description of the Related Art

A search for a comfortable, accurate, and commercially-feasible apparatus to record traumatic head events and other biological and physical occurrences has resulted in numerous attempts. All references disclosed herein are incorporated by reference.

U.S. Pat. No. 5,978,972, for example, describes an acceleration-monitoring device comprising an array of orthogonal accelerometers. It does not describe an intra-oral appliance, nor does it describe any design considerations for data integrity.

U.S. Pat. No. 6,826,509 describes the monitoring of a body part using a plurality of sensors adjacent to the outer surface of the body part with sensing axes orthogonal to the outer surface. It does not describe an intra-oral appliance, nor does it describe any design considerations for data integrity.

U.S. Pat. No. 6,941,952 describes a sensing mouthpiece with at least one linear force sensor for sensing impact forces on the head of the user. It further describes the mouthpiece to have a mouth guard and sensors located on the hard palate. It does not describe where on the hard palate these sensors would be located, nor does it describe how sensors could be located on the hard palate without covering lingual surfaces and diminishing the wearer's ability to communicate. The current invention does not have sensors or any other components in the hard palate area of the oral appliance.

U.S. Pat. No. 8,930,144 describes an apparatus for measuring acceleration of a person's head comprising a sensor and a control unit that determines whether or not to enable recording based on the relation of the measured acceleration and a risk of an acute injury. In aspects of the current invention, an accelerometer itself contains filters, ADC, comparators, and interrupt; a controller is asleep, and an accelerometer interrupt wakes the controller which saves data to non-volatile memory based on the acceleration being identified as an impact exposure including injurious and non-injurious events.

U.S. Pat. No. 9,354,447 describes a head mounted information system comprising a sensor unit including a gyroscope and configured to measure jump or flight time metrics. It does not describe an intra-oral appliance, nor does it describe any design considerations for data integrity.

U.S. Patent Application Publication No. 2011/0184319 describes an instrumented mouthguard with at least two sensors and a processor that determines if the mouthguard is in place using data from one sensor and determining the direction and magnitude of the impact from the other sensor. It does not consider that a minimum of two sensors are required to measure the 6D kinematics of the head, nor does it describe a process of designing or locating the sensors to improve data integrity.

U.S. Pat. No. 8,291,912 describes a method for manufacturing oral-based hearing aids which can be designed based on intra-oral scans and manufactured using 3D printing. Its disclosure is specific to hearing aids, and describes locating the vibrating transducer in contact with a tooth. It does not describe an additional optimization of the sensor location or device dimensions to improve data integrity and user comfort.

Guard Labs (https://www.guardlab.com/pages/about-us) creates custom fitted mouthguards using an intra-oral scanner to collect the wearer's dentition data, then 3D printing is used to create a model of the dentition, and the appliance is thermoformed to the 3D printed model. This company does not include any sensors, electronics, or instrumentation in the devices.

U.S. Patent Application Publication No. 2017/0156635 describes an instrumented mouthguard that is designed such that the sensors are near the front of the mouthguard and a standoff is generated between the molars to isolate the sensors and mitigate noise generated in sensor data from teeth chatter. This application is a generalized design to be applied to all wearers of the device and implements a long-standing design criteria of isolating sensors from noise. It does not however apply this technique in a unique or individual method that would optimize data integrity for each user and consider comfort. Adding material to the occlusal surface of the molars could decrease comfort for wearers, and reduce wearer compliance.

U.S. Patent Application Publication No. 2017/0095204 A1 describes an instrumented oral appliance which is rigidly coupled to the bony portions of the upper jaw comprising a rigid central component and sensor. The application describes obtaining the wearer's dentition data using a negative mold rather than an intra-oral scan. Also, the application describes only that the sensors be centrally located as an assumption that this is where they will be located for all wearers.

SUMMARY

The present invention is an instrumented intra-oral appliance which is computationally designed to optimize the comfort for the wearer as well as the location of sensors to maximize data integrity. This can include the design of a generalized electronics package that will fit the majority of the target population based on a statistical shape analysis. The intra-oral appliance can also be customized for each individual using data collected with an intra-oral scan. The device can also be optimized using finite element analysis. Finally, the device can be manufactured in part or in whole by 3D printing.

The geometry of each person's mouth is unique. In one embodiment, the invention herein teaches an instrumented intra-oral appliance, which is optimized to increase compliance, meaning wearing the appliance, while also enhancing the location of sensors to record an event (e.g., traumatic head impact), or biological sign (e.g., blood oxygen level), or environmental conditions (e.g., amount of carbon monoxide inhaled). Because the interior of the mouth is sensitive to contact, an intra-oral appliance that accounts for mouth geometry to determine where to place certain sensors is needed. The invention described herein teaches a way to computationally optimize the placement of the sensors so that the appliance does not irritate the user. Moreover, because some areas of the mouth are more advantageous to place certain sensors (e.g., a near infrared sensor to record heart rate is best located near a superficial artery), an appliance is taught with such sensors located where they will best perform their functions as determined based on, for example, an intra-oral scan.

Past attempts have taken a one-size-fits-all approach and the result is lack of patient compliance—for example a football player will not wear an instrumented mouth guard that is uncomfortable. Other approaches that have endeavored to make a unique appliance based on the user's dental geometry have not accounted for how differences will affect optimal locations for sensors. The present invention teaches a way to make an intra-oral appliance that resolves the shortcomings of the prior art, by creating an intra-oral appliance that is then computationally analyzed to optimize placement of sensors to increase both user comfort and accuracy of recordings by the sensors.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

FIG. 1 is a picture of a 3Shape Trios intra-oral scanning pod.

FIG. 2 is a diagram of a bottom portion of an intra-oral appliance according the invention described herein, showing the location of certain electronic components.

FIG. 3 are pictures of embodiments of the present invention showing electronic geometries bonded to a layer of the sample and the completed sample with the electronics embedded between layers.

FIG. 4 are pictures of embodiments of the present invention showing electronic geometries and completed samples.

DETAILED DESCRIPTION OF VARIOUS EMBODIMENTS OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties.

Embodiments of the invention also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e. processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g. software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The instrumented intra-oral appliance is designed computationally to optimize the location of sensors to maximize data quality of head kinematics experienced during impact events. The sensors are rigidly coupled to the human head to ensure that they measure the kinematics of the head. Also, the lower mandible can interact with the upper jaw which can cause noise or false events in inertial sensors designed to measure kinematics. The location of the sensors with respect to the lower jaw minimizes noise and false positives created by the upper and lower teeth interacting. Also, the sensors are located within layers of an intra-oral appliance with differing material properties to minimize noise, such as hardness, stiffness, flexural modulus, tensile modulus, and/or tensile strength. These layers are designed such that they have mechanical damping properties that act as a low pass filter to reduce noise and chatter from the upper and lower teeth interacting. The sensors can also be located in proximity to anatomical surfaces with larger flat or nearly flat surfaces to control the thickness of layers and mechanical damping properties of the appliance.

In another embodiment, the sensor may comprise a photoplethysmogram (PPG) or near infra-red (NIR) sensor that is located to minimize noise generated by human motion and ambient light. PPG and NIR sensors need to be placed in close proximity to the body surface and specifically an area with superficial arteries to maximize signal quality. Additionally, NIR and PPG sensors are subject to noise from ambient light, and the sensors, according to the present invention, are placed in an intra-oral appliance such that they are located on a surface that does not have exposure to ambient light during typical use. The device can further be designed such that the sensor is pushed against the body and the appliance creates a seal around it blocking out ambient light. The surface of the appliance in contact may also be designed such that ambient light is blocked from the sensor over a larger area so that the device does not cause discomfort to the wearer. The appliance may also be designed such that the device is rigidly coupled to the dentition to minimize any motion between the appliance and the human body. This minimizes noise generated by motion artefacts (relative motion between the sensor and the body). The appliance may also be designed of multiple layers that incorporate rigid layers for coupling and compliant layers for mechanical damping.

In another embodiment the sensor is a flow meter or air quality sensor that is located to minimize flow resistance or turbulent flow that causes measurement errors. These sensors are typically used in diagnostic devices for sleep apnea and CPAP machines designed to treat such sleep disorders. Placing the sensors into a low profile, minimal volume intra-oral appliance allows for sleep apnea to be detected using a comfortable, at home appliance, eliminating the need of having to undergo an overnight, monitored sleep study at a medical sleep center. The overnight stay at a sleep center is expensive due to the equipment, lab space, and personnel to administer the tests. Such centers also introduce significant research confounding variables by requiring subjects to sleep in a lab. In another aspect, the device taught herein could be implemented in a sleep study lab to eliminate cables and hoses connected to sleep study subjects.

In another embodiment, the previously described sensors could be combined to create a sleep monitor. These sensors are already commercially available in wrist worn activity monitors. Unfortunately, hand and arm motion are not alone indicative of whole body motion. Also, PPG and NIR sensors on a wrist can add to the ambient light in a room, thereby disturbing sleep for the wearer and negatively affecting results.

In another embodiment, strain gauges are located in a retainer or orthodontic aligner in locations of the device that apply forces on the teeth to measure duration and magnitude of the reaction forces on the device. In this implementation, the measured strain in the device is indicative of the force it is applying to the teeth. It is also an indicator that the device is being worn, increasing wearer compliance and thereby improving results. Orthodontic aligners are often designed in a series of aligners from original position to the desired final position with multiple steps between. The wearer changes from one to another based on check-ups with the orthodontist or a prescribed time schedule. By including strain gauges in the aligners, the user would be informed empirically when to change from one aligner to the next based on the amount of strain measured in the aligning appliance. This would reduce the amount of follow-up visits to the orthodontist and could expedite the realignment process by implementing changes empirically and more rapidly with less cost.

In preferred multiple embodiments, aspects of the appliance, such as location and/or placement of the sensors, are optimized computationally. For example, this optimization can be performed using computation finite element analysis or computational fluid dynamics. In one aspect, the appliance surface area is minimized by starting with a standard design applied to the unique device. The standard design, in one example, could be covering the $1^{st}$ and $2^{nd}$ molars bilaterally on the buccal, occlusal, and palatal surfaces up to the gingival margin with only the buccal surface of the remaining teeth covered. This model is placed on the dentition and exposed to 6D kinematics conditions expected during use. The surface area may be reduced by around 200 microns at the gingival margins of the molars and exposed again to the 6D kinematics conditions expected during use. The appliance surface area may be reduced further until a difference in motion between the appliance and the dentition is measured computationally. The same method could be done to optimize material thicknesses or stiffness, physical properties of the appliance, size of the appliance, etc. Although the optimization is a 1-direction optimization, this method could be applied to any type of optimization routine. The optimization routine could also be performed automatically, with receiving the intra-oral geometry and an order for the type of appliance and the output being a final design.

In preferred multiple embodiments, the manufacturing of the appliance is streamlined by the output of the computational design being a digital file that can be sent directly to the manufacturing facility such as an STL file that would be sent to a 3D printing manufacturer for rapid fabrication.

The location of sensors may be identified by locations that are not susceptible to vibrational antinodes in the range of measurement frequencies according to the Finite Element Analysis ("FEA"). Flow sensors may be optimally located using a Computational Fluid Dynamics model to identify locations with minimized turbulence.

Preferred embodiments include the optimization of design to limit noise to sensors. This design may also be conducted using FEA. If a minimum surface area is defined to retain an appliance, the material properties of that appliance, including the potential for multiple layers may be modified to tune the appliance to specific frequency content of the data the sensors are collecting. Additionally, the data may be tuned to be a filter for known noise frequencies. For example, the material around a PPG sensor could be tuned to reject mechanical noise below 1 Hz, which corresponds to a breathing rate of 60 breaths/min. Using a mechanical filter to minimize motion of the sensor allows heart rate data to be collected at 1 Hz, while rejecting noise from breathing at the same frequency. This is especially important in that the noise cannot be filtered from the data itself.

In some embodiments of the invention, the 3D anatomical geometries of the wearer are collected using an intra-oral scanner. There are numerous models of intra-oral scanners including but not limited to: 3M True Definition Scanner, 3 Shape Trios 3 Scanner, or Carestream Dental CS 3600. These scanners take a series of photographs of a subject's dentition, interleave the pictures together, and generate a 3D digital model of the subject's dentition. Some scanners are color, and this color provides visual indication of sensitive areas of the gingiva indicated by redness. Although the color scanners provide additional data, monochrome intra-oral scanners can collect 3D anatomical geometries as well.

Although an intra-oral scanner provides the most accurate measurement of the anatomical geometries, a traditional impression of the dentition can be taken with alginate, PVS or other products. Since intra-oral scanning is a more direct means of measurement, it is preferred but not required.

Intra-oral appliances can be designed and manufactured using only the upper or lower dental 3D anatomical geometries, on which the appliances will be mounted. However, additional data may be collected from the opposing dentition and bite alignment that can be used to improve the fit of an intra-oral appliance. Collecting the opposing dentition 3D geometry and a bite alignment allows the occlusal surface of the device to be designed to most comfortably fit when teeth are closed, clenched, or closed on an appliance. This technique can further be implemented to alter the bite of a wearer in appliances such as anti-snoring and sleep apnea prevention appliances. The opposing dentition and bite alignment data can be collected directly using an intra-oral scanner, or it can be collected using impressions and bite trays which are later scanned.

Intra-oral appliances defined herein may be manufactured with existing biocompatible materials that currently exist or those that may be created and appropriate for intra-oral appliances. Currently existing possibilities include, but are not limited to, standard thermoformable materials such as EVA, acrylic, PET-G, etc., as well as branded products that contain these materials including, but not limited to, Polyshok, Dura-soft, Duran, etc.

In a preferred embodiment, the appliances are manufactured using 3D printing methods. There are existing biocompatible 3D printing materials that have been developed for the dental industry. One company, for example, Next Dent, has an extensive list of products such as Base, Surgical Guide, Crown and Bridge, Ortho Rigid, Ortho Clear, Ortho IBT, Dental Model, Model Ortho, Tray, Gingiva Mask, Cast, and Crown and Bridge MFH. Other companies, such as FormLabs, also have 3D printable resins for the dental industry including Model Resin, Surgical Guide, LT Clear, Denture Base, and Denture. These are only a few examples of 3D printing materials that are currently available for the dental industry.

In a preferred embodiment, the appliances are manufactured by a combination of 3D printing and thermoforming. In aspects, depending on the computational optimization, the design comprises multiple layers. One rigid, 3D printed layer is designed with recesses to optimally place the electronics and sensors. The electronics and sensors may be bonded to said layer using 2 part acrylic, such as Ortho Jet acrylic (Lang Dental Mfg. Co., Inc., Wheeling, Ill.), light curing acrylic such as Orthocryl LC (Dentaurum GmbH & Co. KG, Ispringen, Germany), or other biocompatible bonding components. The rigid, 3D printed layer could be adjacent to the wearer's dentition, or offset by a thermoformed layer. Again, the 3D printed layer could be in contact with the opposing dentition or it could have a layer thermoformed over top of it. The design of the device, including the thickness, size, geometries, and other physical aspects of each layer may be optimized and designed computationally. Furthermore, the dental model may be modified computationally based on the appliance design to accommodate thermoforming to an idealized dental model. The changes may include build-ups around diseased or sensitive areas, the inclusion of cut lines that correspond to design criteria, or other features that improve the design or manufacture of the appliance. Other bonding materials could include food grade and medical device grade room temperature vulcanizing (RTV) materials such as Dow 748.

The devices may also be manufactured by 3D printing negative molds for the appliance and using other techniques such as injection molding. This method requires an additional step to the process, but the location of the electronics and the design of the appliance can still be performed computationally. Also, the geometry of the device including thickness, volume area, contact points, etc. can still be optimized computationally. The benefit of this method is the additional biocompatible materials that are available to injection molding as compared to 3D printing.

Although thermoforming and 3D printing are defined herein, these are the current manufacturing techniques used in the dental industry. However, the inventions do not require these specific manufacturing processes and can be applicable to manufacturing techniques that are appropriate for making intra-oral appliances according to the present invention.

The design of the appliance can be conducted with boundary conditions that are defined by the American Dental Association and the European Committee for Standards, and these standards are incorporated herein by reference. These standards define minimum material thicknesses and coverage to provide sufficient protection. These boundary conditions could be included as inputs to the computational design of the appliance such that the appliances meet the appropriate standard, but they do not include additional material thickness, volume, or surface area.

Another manner to apply boundary conditions to the appliance is to provide a non-functional sample to the wearer. The material provided would have similar material properties such as hardness and flexural strength, but be easy enough to trim by the wearer or someone administering the non-functional appliance. The wearer would be allowed to modify the appliance as desired to their comfort. Once the appliance is trimmed to the user's preference, it may be 3D scanned. The resulting 3D volume is used as a design envelope for the functional appliance.

Other boundary conditions include the depth of electronic components such as an inductive charging coil. These components are prevalent in consumer electronics, and allow for the wireless charging of an electronic device. Unfortunately, smaller coils are more dependent on alignment of the inductive coil with its partnering coil in the charger device. Misalignment of the inductive coils can cause increased battery charging times and data transmission times if the coil is also being used for transferring data. Worse yet, the misalignment of the coil can cause the generation of heat, which could damage the appliance itself especially if made in part from thermoformed materials. The device could be designed such that the location of the coil is defined exactly in depth, location, and orientation such that it mates with a charging station with minimal possibility for error.

The location of sensors and electronics may be determined based on available surface area in the anatomical geometry such that rigid electronics and sensor components fit within the appliance design area and volume. Additionally, a statistical shape analysis may be performed on anatomical geometry data collected from a target population. The SSA outputs features of the anatomical geometry that account for the variance within the target population. The SSA can provide mean geometry, extremes, and $5^{th}$ and $95^{th}$ percentile geometries. These data can be used as design constraints for the electronics such that the distance between rigid components or boards is optimized such that it will fit both the smallest and largest anatomies within the population. One implementation of this is having a set distance between the electronic components, the location of the largest component would define where the electronics are coupled to the rigid layer, and the wearer would have choices of which version they preferred.

Example 1

The first example comprises at least one rigid layer. Such a layer includes recesses that accept the electronics geometries (FIG. 2). In this example, the computational optimization determines, based, for example, on surface geometry of the dentition, that the battery is optimally placed between the 1st and 2nd molar on palatal surface of the left side (2010 in FIG. 2). The main circuit board is optimally placed behind the middle incisors (2020), and the power circuit board is placed on the palatal side of the 1st and 2nd molar on the right side (2030). These locations are defined as optimal by calculating the volume of material required around each component to maintain a smooth palatal surface while maintaining minimum material thickness. The appliances may be 3D printed and then cured, if necessary. Once the appliance is printed, the electronics are attached and the appliance may be custom trimmed (see FIG. 3, 3010). This device is designed such that the rigid layer is in direct contact with the teeth. In this example, a layer of EVA is thermoformed over the rigid layer while placed on the dentition. The EVA is trimmed to cover the dentition (3020).

Example 2

In this example (see FIG. 4), the intra-oral scan provided visual evidence of sensitivity on the gingival margin on the palatal surface of the teeth. It is computationally determined that the optimal location for the electronic components are to be bonded to the buccal surface of the rigid layer with a battery on the right side, the main circuit board in front of the middle incisors, and the power circuit board on the left (4010). The 2nd example has a layer of EVA in contact with the teeth and gingiva to mitigate irritation to diseased gingival tissue, then the rigid layer, and finally a layer of EVA is thermoformed over the top and trimmed.

Example 3

In this example (see FIG. 4), it is determined that based on the user's dentition geometry having a small distance across the width of the palate and molars with larger exposed height, that comfort of the user can be optimized by a combination of electronics component selection and placement. With a small palate width, components placed on the palatal surface will interact more with the tongue and negatively influence speech. Therefore, the power circuit board is optimally placed in the same position as in the second example, on the buccal surface. The main circuit board is located on the buccal surface of the right first molar. The battery can be located as in the first and second example but being replaced with a thinner, wider battery geometry, which fits within the palatal surface of the first and second molars without interacting with the tongue due to the reduced height. (4020). Accordingly, different electronic components may be chosen, including by computer model, based on the determined geometry and physical aspects of the intra-oral appliance according to, for example, an intra-oral scan. A third example has a layer of EVA in contact with the teeth and gingiva, then the rigid layer, and finally a layer of EVA is thermoformed over the top and trimmed.

Example 4

In this example, the appliance is designed to mitigate motion between the appliance and the user's dentition to facilitate the accurate recording of head kinematic data. The electronic components will be located within the appliance to minimize the appliance as in the first example, with the addition of placing the electronic components within the appliance as proximal to the dentition as possible to minimize the potential for inertial differences between the electronics components and the dentition. The appliance is further designed such that the rigid layer which contains the electronic components acts as a calibrated mechanical spring retention system by covering the buccal, occlusional, and palatal surfaces of teeth beyond the widest point of the tooth. The standoff distance of this rigid layer can be designed to accommodate direct contact with the teeth, with the material thickness at the buccal-occlusional intersection and the palatal-occlusional intersection defining the mechanical spring strength for a material.

Example 5

In this example, the appliance is designed with a compliant layer between dentition and the rigid layer, whereby the rigid layer of the appliance is designed with known standoff distances from the dentition to allow for the compliant layer to be thermoformed to the dentition, and the rigid layer to be bonded to the thermoformed compliant layer, where the bonding of the rigid layer occurs during latter stages of thermoforming allowing the rigid layer to modify a relatively uniform thickness thermoformed layer to fill the computationally designed standoff volume between the dentition and rigid layer, which do not have a uniform standoff distance.

Example 6

In this example, the size of the appliance is optimized computationally by defining anatomical markers such as largest width of a tooth and crowded, overlapping teeth that act as retention points for an appliance. The appliance is designed to cover, for example, a minimum of three retention points, with the prevalence of retention points exceeding the minimum, the three retention points that are connected by the minimal amount of material while providing sufficient surface area for mounting the electronics components are chosen.

Example 7

In this example, the distance between electronics components are first defined by performing a statistical shape analysis on the 3D anatomical data collected from a target population, which defines the smallest and largest length of the population's upper dentition arch from the palatal surface of tooth 2 and 15 so that a generalized electronics design can be generated which spaces the components far enough away from one another to allow the electronics to conform to the user's dentition without exceeding the shortest arch defined above. The generalized electronics design would then be located within each individual appliance by placing the largest component, the battery for example, in a location that has a surface area most suited for mounting it which would minimize the volume required to retain the electronics and maintain a smooth surface.

Example 8

In this example, a bleaching tray contains reservoirs of a chemical teeth bleaching agent and at least one strain responsive mechanical valve. The appliance would be designed such that the act of placing the appliance over the dentition would induce strain in the appliance. The appliance design would further have strain activated mechanical valves located where the strain would be generated in the appliance. These valves would open each time the appliance was placed on the dentition allowing a controlled amount of chemical teeth bleaching solution to be released.

Example 9

In this example, a chemical agent is contained in a reservoir within the appliance that is a therapeutic treatment for an acute injury such as mild traumatic brain injury. This chemical agent is combined with inertial sensors that measure the kinematics of the wearer's head. When the inertial sensors measure head kinematics that are potentially injurious, the device would release the chemical agent as an initial therapeutic treatment.

Example 10

In this example, a dental implant is created with electronics built within the structure of the tooth. The outer geometry of the implant matches the subject's existing anatomical geometry and the interior is designed to accept the electronics package. The electronics are activated by placing an appliance over the dental implant, and the appliance has an inductive coil to provide power to the appliance and transfer data between the implant and the appliance.

Example 11

In this example, a retainer contains electronics to measure breathing rate and volume and a reservoir of a biological agent such as epinephrine. If the wearer has a severe allergic reaction their breathing will drastically reduce in volume and increase in rate. If the sensors detect this life threatening event, they signal the reservoir to dispense the biological agent to the wearer, preventing their death.

Example 12

In this example, an appliance design is optimized to meet a minimum performance threshold. The inertial sensors in the appliance have a frequency response from 1-1000 hz, and the appliance structure around the electronics has a natural frequency. The minimum performance threshold for the appliance structure is a natural frequency 4× the maximum sensor frequency response (4000 hz). The appliance would be iteratively designed with this minimum performance threshold as a pass/fail criteria.

Example 13

In this example, an appliance is designed to heal the patient after an injury or surgery. The appliance is designed to match the wearer's anatomical geometry, with the recesses adjacent to a damaged portion of the wearer's intra-oral cavity that contain tissue like an allograph. The appliance has mechanical retention and holds the allograph in place. The bond between the allograph and remainder of the appliance degrade consistent with the timeline for the allograph to bond to the damaged area of the intra-oral cavity.

Example 14

In another example, the electronics may be embedded between two rigid layers with a flexible potting material (RTV) between the layers that bonds the layers together and protects the electronics. This design can be designed or thermoformed adjacent to the dentition with an overmold of EVA. It can also be designed or thermoformed between two layers of EVA. In either case, as the mouthguard wears from use and abuse by the user, the rigid case and electronics within can be removed from the EVA and reused with newly thermoformed EVA. This reduces the cost and time required to replace mouthguards damaged during normal use.

In this example, the appliance is designed computationally using 3 Shape appliance designer, Meshmixer, Blender, Netfabb Basic, or another CAD software. The base layer of the appliance is defined by minimum coverage area to achieve retention and cover the electronics, a minimum thickness, standoff distance from the dentition model, and any blockout areas. The 3D electronics models are then placed on the surface of the appliance base layer. The 3D electronics model is manipulated to minimize the space between itself and the appliance base layer minimizing the size of the appliance. Once the optimized location of the electronics has been identified, any space between the appliance base layer and the electronics is filled. Then an overlayer is designed to a specific thickness to cover the electronics and appliance base layer. The overlayer and appliance base layer 3D models are merged computationally with the resulting 3D model defining the optimized volume of the appliance which can be used to create a negative mold for injection molding.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of designing an oral appliance, the steps comprising:

Providing one or more 3D models of all or a portion of an oral cavity;

Providing one or more 3D models of one or more electronic, chemical, biological, and/or mechanical oral appliance components;

Executing with a computer processor a computer-executable program for selecting placement in or on an oral appliance of one or more of the electronic, chemical, biological, and/or mechanical oral appliance components based on one or more parameters obtained from said 3D models; and Forming the oral appliance based on results of the placement selecting and according to one or more of the following criteria:
  a fitting of the oral appliance in the oral cavity;
  placement of the one or more electronic, chemical, biological, and/or mechanical oral appliance components in or on the oral appliance; and/or
  maintaining functionality of the oral appliance;

wherein the one or more 3D models of all or a portion of the oral cavity and/or the one or more electronic, chemical, biological, and/or mechanical oral appliance components provide sufficient detail to identify one or more surface level medical conditions, including gingivitis, skin cancer, broken dentition, and/or other medical conditions; and wherein the oral appliance is designed to avoid contact with surface level medical conditions to increase user comfort, or designed to contact surface level medical conditions to increase contact for enhanced medical treatment.

2. A method of designing an oral appliance, the steps comprising:

Providing one or more 3D models of all or a portion of an oral cavity;

Providing one or more 3D models of one or more electronic, chemical, biological, and/or mechanical oral appliance components;

Executing with a computer processor a computer-executable program for selecting placement in or on an oral appliance of one or more of the electronic, chemical, biological, and/or mechanical oral appliance components based on one or more parameters obtained from said 3D models;

Accounting for oral features of a wearer to provide user comfort and compliance with intended use of the oral appliance; and Forming the oral appliance based on results of the placement selecting and according to one or more of the following criteria:
  a fitting of the oral appliance in the oral cavity;
  placement of the one or more electronic, chemical, biological, and/or mechanical oral appliance components in or on the oral appliance; and/or
  maintaining functionality of the oral appliance.

3. A method of designing an oral appliance, the steps comprising:

Providing one or more 3D models of all or a portion of an oral cavity;

Providing one or more 3D models of one or more electronic, chemical, biological, and/or mechanical oral appliance components;

Executing with a computer processor a computer-executable program for selecting placement in or on an oral appliance of one or more of the electronic, chemical, biological, and/or mechanical oral appliance components based on one or more parameters obtained from said 3D models;

Providing one or more components for recording, analyzing, and/or transmitting data that is generated by one or more sensors in or on the oral appliance and, based on the data, providing instructions to the one or more electronic, chemical, biological, and/or mechanical oral appliance components incorporated in or on the oral appliance; and Forming the oral appliance based on results of the placement selecting and according to one or more of the following criteria:
  a fitting of the oral appliance in the oral cavity;
  placement of the one or more electronic, chemical, biological, and/or mechanical oral appliance components in or on the oral appliance; and/or
  maintaining functionality of the oral appliance.

4. A method of designing an oral appliance, the steps comprising:

Providing one or more 3D models of all or a portion of an oral cavity;

Providing one or more 3D models of one or more electronic, chemical, biological, and/or mechanical oral appliance components;

Executing with a computer processor a computer-executable program for selecting placement in or on an oral appliance of one or more of the electronic, chemical, biological, and/or mechanical oral appliance components based on one or more parameters obtained from said 3D models;

Providing a fitting algorithm for classes of oral appliances using statistical shape analysis to determine bounds for allowable placement and/or positioning in or on the oral appliance of the electronic, chemical, biological, and/or mechanical oral appliance components, including variances within said bounds for the oral appliance and/or a wearer of the oral appliance; and Forming the oral appliance based on results of the placement selecting and according to one or more of the following criteria:
  a fitting of the oral appliance in the oral cavity;
  placement of the one or more electronic, chemical, biological, and/or mechanical oral appliance components in or on the oral appliance; and/or
  maintaining functionality of the oral appliance.

5. A method of forming an oral appliance that combines electronic and structural elements, the steps comprising:

Providing at least one 3D model of at least a portion of an oral cavity;

Providing at least one 3D model of at least one electronic element chosen from a processor, a sensor, a data storage device, and/or a power source;

Executing with a computer processor a computer-executable program for:
  Identifying spatial and/or sizing parameters from the 3D models for fitting an oral appliance in the oral cavity;
  Based on parameters obtained from the 3D models, selecting placement in or on the oral appliance of at least one electronic element, which placement is selected to minimize the volume and/or size of the oral appliance; and
  Creating from the 3D models a structural element geometry for the oral appliance based on the fitting of the oral appliance in the oral cavity and placement of the at least one electronic element in or on the oral appliance.

6. A method of creating an instrumented intra-oral appliance, the steps comprising:
Scanning at least a portion of an oral cavity;
Generating a 3D model of the oral cavity;
Executing with a computer processor a computer-executable program for
formulating one or more intra-oral appliance design geometries based on the 3D model of the oral cavity;
placing one or more electronic components in a selected location of the intra-oral appliance design based on the geometries of the intra-oral appliance;
Forming an instrumented intra-oral appliance, with the one or more electronic components integrated therein, from the intra-oral appliance design geometries, for a user wherein the intra-oral appliance conforms to a user's mouth; and
Providing the user with one or more design options of the instrumented intra-oral appliance and allowing the user to choose one or more design options, providing the user with the instrumented intra-oral appliance the user can cut down, trim, or otherwise modify, reducing pressure on all or a portion of a user's dentition by spreading forces from the instrumented intra-oral appliance, forming the instrumented intra-oral appliance so as not to influence or interfere with speech or interact with a user's tongue, and/or matching parts on the instrumented intra-oral appliance to existing geometries to limit or decrease a volume of the instrumented intra-oral appliance.

7. A method of creating an instrumented intra-oral appliance, the steps comprising:
Scanning at least a portion of an oral cavity;
Generating a 3D model of the oral cavity;
Executing with a computer processor a computer-executable program for
formulating one or more intra-oral appliance design geometries based on the 3D model of the oral cavity;
placing one or more electronic components in a selected location of the intra-oral appliance design based on the geometries of the intra-oral appliance; and
Forming an instrumented intra-oral appliance, with the one or more electronic components integrated therein, from the intra-oral appliance design geometries, for a user wherein the intra-oral appliance conforms to a user's mouth;
wherein the instrumented intra-oral appliance is formed to minimize recording false positives of possible traumatic head impacts and/or mitigate data artifacts caused by human motion and other external interferences.

8. A method of designing an oral appliance that combines electronic and structural elements, the steps comprising:
Providing at least one digitized rendition of at least a portion of an oral cavity;
Providing at least one digitized rendition of at least one electronic element;
Identifying parameters that insure a comfortable fit of the oral appliance in the oral cavity;
Identifying a minimum performance threshold for the at least one electronic element; and
Electronically manipulating the digitized renditions to arrive at a structural element geometry for the oral appliance designed to balance the parameters that allow for a comfortable fit with the minimum performance threshold.

9. The method of claim 5, wherein the placement in or on the oral appliance of the at least one electronic element is based on reaching a minimum performance threshold for the at least one electronic element.

10. The method of claim 5, wherein the placement in or on the oral appliance of the at least one electronic element is based on fitting of the oral appliance in the oral cavity and the function of the at least one electronic element.

11. The method of claim 5, wherein the at least one electronic element is configured to not transmit data to an electronic device separate from the oral appliance while the oral appliance is in use or being worn.

12. The method of claim 5, wherein the data storage device is configured such that data stored on the oral appliance is capable of being accessed by an electronically paired electronic device.

13. The method of claim 5, wherein the at least one electronic element is configured to not notify a wearer, observer, coach, parent, or another device separate from the oral appliance while the oral appliance is in use or being worn.

* * * * *